United States Patent [19]
Young

[11] Patent Number: 5,409,003
[45] Date of Patent: Apr. 25, 1995

[54] PROBES FOR USE IN IMAGING

[75] Inventor: Ian R. Young, Marlborough, England

[73] Assignee: Picker International, Inc., Highland Hts., Ohio

[21] Appl. No.: 227,575

[22] Filed: Apr. 14, 1994

Related U.S. Application Data

[63] Continuation of Ser. No. 972,421, Nov. 5, 1992, abandoned.

[30] Foreign Application Priority Data

Nov. 22, 1991 [GB] United Kingdom ............... 9124810

[51] Int. Cl.⁶ ............................................. A61B 5/055
[52] U.S. Cl. ............................... 128/653.2; 128/653.5
[58] Field of Search .......... 128/653.2, 653.5, 749–759, 128/642; 601/46

[56] References Cited

U.S. PATENT DOCUMENTS

| | | | |
|---|---|---|---|
| 4,245,653 | 1/1981 | Weaver | 128/756 |
| 4,672,972 | 6/1987 | Berke . | |
| 4,932,411 | 6/1990 | Fritschy et al. | 128/653.2 |
| 5,035,231 | 7/1991 | Kubokawa et al. | 128/653.5 |
| 5,211,166 | 5/1993 | Sepponen | 128/653.5 |
| 5,215,088 | 6/1993 | Normann et al. | 128/784 |

FOREIGN PATENT DOCUMENTS 64-65451  3/1989  Japan ................................ 128/749

OTHER PUBLICATIONS

Nuclear Magnetic Resonance Microscopy with 4–μm Resolution: Theoretical Study and Experimental Results; Cho, et al.; Medical Physics, vol. 15 No. 6, Nov./Dec., 1988, pp. 815–824.

Primary Examiner—Ruth S. Smith
Attorney, Agent, or Firm—T. B. Gurin; R. A. Notzen

[57] ABSTRACT

A probe (3) for use in in vivo imaging of a microscopic internal region (1) of a patient's body using magnetic resonance techniques incorporates a member (7) having a surface having a pattern of projections (9) formed thereon. In use the surface contacts the surface of the region to trap between the projections molecules in the region, thereby to restrict diffusion of the molecules and so improve resolution of the image obtained.

9 Claims, 1 Drawing Sheet

PROBES FOR USE IN IMAGING

This is a continuation of application Ser. No. 07/972,421, filed on Nov. 5, 1992, now abandoned.

BACKGROUND OF THE INVENTION

This invention relates to probes for use in imaging and, in particular, to probes for use in in vivo imaging of microscopic internal regions of a patient's body using magnetic resonance techniques.

In some conventional systems for in vivo imaging of internal tissues, a probe is inserted into a channel, normally a naturally-occurring channel, in the body to collect signals representative of the tissue surface to be imaged, and pass the signals to image processing means.

Where the regions to be imaged are microscopically small e.g. of diameter of no more than 1.5 mm, it is difficult to achieve satisfactory resolution.

When using magnetic resonance imaging techniques, the problem arises that water molecules have a diffusion coefficient of around $3.5 \times 10^{-3}$ mm$^2$/s at 37° C. in bulk water and the diffusion coefficient of water molecules in body tissue is likely to be much the same. In imaging systems, the time interval between RF excitation of a region and magnetic resonance data acquisition is of the order of 10 ms. Hence, half of the molecules originally excited in one part of the body tissue will have diffused over a distance of around 8 microns before their signals are acquired. Reducing the time interval between excitation and data acquisition requires wider acquisition bandwidths to be used, thus decreasing the signal to noise ratio, and also makes it necessary for stronger spatially encoding gradients to be used. Localised cooling of tissue may slow down diffusion, but this produces only a minor reduction in diffusion before the water molecules begin to form ice.

It is an object of the present invention to provide probes for use in in vivo imaging of a microscopic internal region of a body in which the above mentioned problems are alleviated.

SUMMARY OF THE INVENTION

According to the present invention, there is provided a probe for use in in vivo imaging of a microscopic internal region of a patient's body incorporating a member having a surface adapted to contact said region in use of the probe, said surface being provided with a pattern of projections dimensioned and spaced from one another such that said projections restrict the diffusion of molecules in said region when said surface contacts said region.

The invention also provides a method for in vivo imaging of a microscopic internal region of a patient's body comprising:
positioning adjacent said region a probe incorporating a member having a surface provided with a pattern of projections;
causing said surface to contact said region; and
producing an image of said region while contacted by said surface using a magnetic resonance technique.

One embodiment of a probe according to the invention and a method of imaging using the probe will now be described by way of example with reference to the accompanying drawings.

DESCRIPTION OF THE PREFERRED EMBODIMENT

Figure 1:
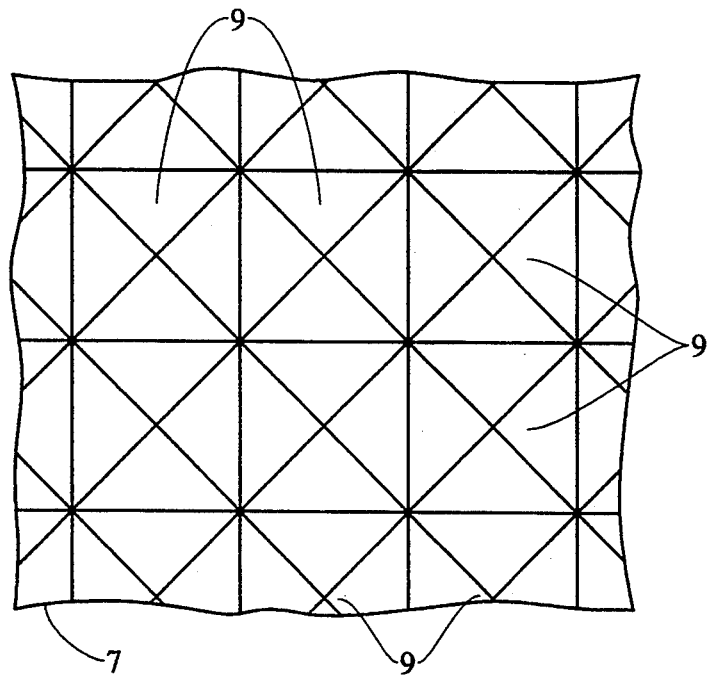
FIG. 1 is an enlarged plan view of part of the probe.

Magnetic resonance imaging of an internal region 1 of a patient's body is carried out using a probe 2 having a cylindrical housing 3 which is formed from a non-reactive metal such as stainless steel. The housing 3 is typically 100 mm long with a diameter of 2.5 mm extending over at least 25 mm of its length from one end. The housing 3 at this end has a compartment 5 closable by a removable cover 6. Within the compartment there is a glass plate 7 having a regular pattern of projections 9 formed on one side thereof. The patterned surface of the plate 7 is urged towards the cover 6 by a spring means 8 in the compartment 5. As shown in FIG. 1, the projections 9 each have the shape of a square pyramid with equal base dimensions and height, typically of 1 micron. The projections 9 are suitably formed by cutting a first set of identical contiguous V-shaped grooves, 1 micron in width and 1 micron deep extending in one direction over the surface of the glass plate 7 and then cutting a further set of grooves which have the same dimensions as the first set of grooves but extend in a direction perpendicular to the direction of the first set of grooves. V-shaped grooves are thus formed between the projections 9.

Figure 2:
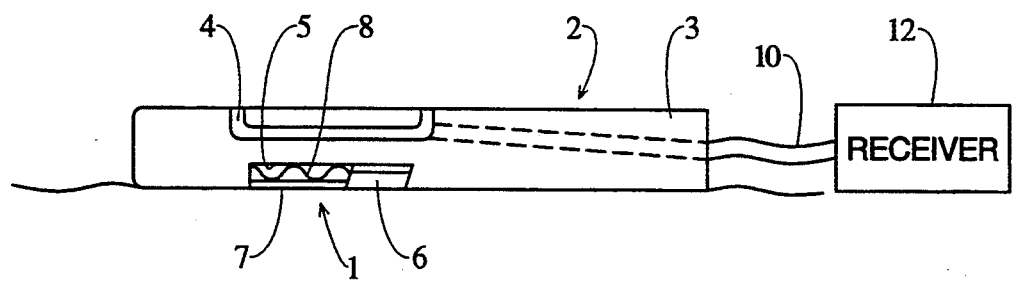
FIG. 2 is a diagram illustrating the probe of FIG. 1 in use for imaging.

The housing 3 is inserted into the body via a natural channel until the cover 6 of the housing 3 is adjacent the region 1 to be imaged, as shown in FIG. 2.

When the cover 6 is removed by sliding axially along the housing 3, the cover 6 being shown partially removed in FIG. 2, the plate 7 is urged into contact with the surface of the region 1 by the spring means 8 so that the projections 9 contact the region 1. Movement of water molecules at the contacted surface of the region 1 is in consequence restricted. The molecules are consequently less likely to diffuse over distances greater than the separation of the apexes of adjacent projections 9 i.e. 1 micron. Thus, a greater proportion of the molecules diffuse over a distance less than 1 micron than would be the case if the surface of the plate were smooth and the molecules could diffuse freely. The hydrogen protons of the water molecules are excited to magnetic resonance in known manner, when the housing 3 is in position, and the resonance signals produced by the protons in region 1 are detected e.g. by coils 4 mounted on the housing 3. These signals are passed via a lead 10 to a processor 12 for use in known manner to produce an image of the region 1.

By restricting the free diffusion of the water molecules and hence the hydrogen protons therein, the movement of the protons during the time interval between excitation and data acquistion is reduced and the resolution of the image produced using the hydrogen proton resonance signals is improved.

It will be appreciated that the projections 9 may have any shape and spacing so long as their dimensions and spacing from one another are such that the overall average diffusion of the particles excited to magnetic resonance is restricted to such an extent that satisfactory resolution is achieved.

In some applications, the resolution achieved is substantially unaffected by diffusion in a direction normal to the probe surface. In such applications, even if the depth of the recesses between the projections exceeds the maximum diffusion length for satisfactory resolution, this will not affect the resolution of the image. Thus in such applications, the projections 9 may be square pyramids whose height is considerably larger than their base length.

It will be appreciated that although the pyramid shaped probe projections 9 as described above can reduce diffusion to an extent which permits adequate resolution to be achieved, diffusion can be reduced still further by using projections shaped to define between them recesses of a more closed form so that the water molecules cannot easily move from one recess to another, the dimensions and spacing of the projections and hence the recesses being chosen such that the maximum diffusion length of the molecules is sufficiently small as to allow satisfactory resolution to be achieved. However, projections of this type are clearly more difficult to form than the pyramidal projections 9 described above.

I claim:

1. A probe for use in in vivo magnetic resonance imaging of a microscopic internal region of a patient's body comprising:
   a housing;
   a member, mounted to said housing, said member having a surface adapted to contact said region in use of the probe, said surface having a pattern of projections, each projection defining an apex, the projections being dimensioned and spaced from one another so as to restrict the diffusion of water molecules in said region to distances less than the separation of the apexes of adjacent projections during magnetic resonance imaging of said region when said surface contacts said region.

2. A probe as claimed in claim 1 wherein said projections are contiguous pyramids.

3. A probe as claimed in claim 1 wherein said housing includes a compartment in which said member is mounted, said compartment having a removable cover to protect said member during positioning of said probe adjacent said region.

4. A probe as claimed in claim 3 further comprising resilient means arranged to urge said member out of said compartment, thereby to bring said surface of said member into contact with said region when said cover is removed.

5. A magnetic resonance imaging apparatus comprising:
   a member having a surface comprising a pattern of rigid projections;
   means for positioning said member adjacent to an internal region of a patient's body;
   means for causing said surface to contact said region; and
   means for producing an image of said region while contacted by said surface using a magnetic resonance technique,
   said projections being dimensioned and spaced from one another such that they restrict the free diffusion of water molecules along a surface of said region in contact with the surface of said member during the production of the image of said region.

6. The apparatus as set forth in claim 5 wherein said projections are contiguous pyramids.

7. The apparatus as set forth in claim 5 wherein said positioning means includes a probe having a compartment in which said member is mounted.

8. The apparatus as set forth in claim 7 wherein said probe includes a removable cover for covering the compartment for protecting said member during positioning.

9. A method for in vivo magnetic resonance imaging of a microscopic internal region of a patient's body comprising:
   positioning adjacent said region a probe comprising a member having a surface on which there is a pattern of projections;
   causing said surface to contact said region; and
   producing an image of said region while contacted by said surface using a magnetic resonance technique, said projections defining grooves between adjacent projections, said grooves and projections restricting the diffusion of water molecules along a surface of said region to a distance less than the separation between adjacent projections during magnetic resonance imaging.

* * * * *